(12) United States Patent
Hössel et al.

(10) Patent No.: US 7,422,735 B1
(45) Date of Patent: Sep. 9, 2008

(54) USE OF CROSSLINKED CATIONIC POLYMERS IN SKIN COSMETIC AND DERMATOLOGICAL PREPARATIONS

(75) Inventors: Peter Hössel, Schifferstadt (DE); Kristin Tiefensee, Westheim (DE); Axel Sanner, Frankenthal (DE); Reinhold Dieing, Schifferstadt (DE); Michael Gotsche, Aachen (DE); Katrin Zeitz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 680 days.

(21) Appl. No.: 09/604,001

(22) Filed: Jun. 26, 2000

(30) Foreign Application Priority Data

Jun. 29, 1999 (DE) ............................ 199 29 758

(51) Int. Cl.
- A61K 8/81 (2006.01)
- A61K 8/00 (2006.01)
- A61K 31/74 (2006.01)
- A61K 31/785 (2006.01)
- A61K 31/79 (2006.01)
- C08F 26/10 (2006.01)

(52) U.S. Cl. .................. 424/70.15; 424/47; 424/78.03; 424/78.22; 424/78.24; 514/937; 526/264

(58) Field of Classification Search .............. 424/70.15, 424/78.03, 47, 78.22, 78.24; 526/304, 264; 514/937

See application file for complete search history.

(56) References Cited

U.S. PATENT DOCUMENTS

| | | | |
|---|---|---|---|
| 4,058,491 A | 11/1977 | Steckler et al. | 260/2.2 |
| 4,348,380 A | 9/1982 | Jacquet et al. | 424/47 |
| 4,402,936 A | 9/1983 | Okumura et al. | 424/70 |
| 4,451,582 A | 5/1984 | Denzinger et al. | 521/38 |
| 4,528,321 A | 7/1985 | Allen et al. | 524/761 |
| 4,542,175 A | 9/1985 | Fink et al. | 524/516 |
| 4,806,345 A | 2/1989 | Bhattacharyya | 424/70 |
| 4,841,066 A | 6/1989 | Goertz et al. | 548/335 |
| 4,859,756 A | 8/1989 | Goertz et al. | 526/263 |
| 5,094,867 A | 3/1992 | Detering et al. | 426/271 |
| 5,219,969 A * | 6/1993 | Uhl et al. | 526/304 |
| 5,275,809 A | 1/1994 | Chen et al. | 424/70 |
| 5,296,218 A | 3/1994 | Chen et al. | 424/70 |
| 5,321,110 A * | 6/1994 | Shih | 526/264 |
| 5,468,477 A * | 11/1995 | Kumar et al. | 424/401 |
| 5,480,934 A | 1/1996 | Messner et al. | 524/458 |
| 5,603,926 A | 2/1997 | Matsumoto et al. | 424/70.15 |
| 5,608,021 A | 3/1997 | Uchiyama et al. | 526/610 |
| 5,609,862 A | 3/1997 | Chen et al. | 424/70 |
| 5,869,032 A * | 2/1999 | Tropsch et al. | 424/70 |

FOREIGN PATENT DOCUMENTS

| | | |
|---|---|---|
| CA | 2151770 | 12/1995 |
| DE | 544 158 | 5/1993 |
| DE | 42 13 971 | 11/1993 |
| DE | 196 26 657 | 1/1998 |
| DE | 197 31 907 | 1/1999 |
| DE | 197 49 618 | 5/1999 |
| EP | 687 694 | 12/1995 |
| EP | 893 117 | 1/1999 |
| EP | 913 143 | 5/1999 |
| WO | WO 93/22358 | 11/1993 |
| WO | WO 93/25595 | 12/1993 |
| WO | WO 96/26229 | 8/1996 |
| WO | WO 96/37525 | 11/1996 |
| WO | WO 97/35544 | 10/1997 |

\* cited by examiner

*Primary Examiner*—Michael G. Hartley
*Assistant Examiner*—Blessing M Fubara
(74) *Attorney, Agent, or Firm*—Novak Druce + Quigg LLP

(57) ABSTRACT

The invention relates to the use of at least one copolymer obtainable by (i) free-radically initiated copolymerization of a monomer mixture comprising
 (a) 1 to 99.99% by weight of at least one monomer chosen from N-vinylimidazoles and diallylamines optionally in partially or completely quaternized form;
 (b) 0 to 98.99% by weight of at least one neutral or basic water-soluble monomer which is different form (a);
 (c) 0 to 50% by weight of at least one unsaturated acid or unsaturated anhydride,
 (d) 0 to 50% by weight of at least one free-radically copolymerizable monomer which is different from (a), (b) or (c); and
 (e) 0.01 to 10% by weight of at least one monomer which acts as crosslinker and has at least two ethylenically unsaturated, nonconjugated double bonds; and
(ii) subsequent partial or complete quaternization or protonation of the polymer in the case where the monomer (a) is unquaternized or only partially quaternized, as additive for skin cosmetic and dermatological preparations.

15 Claims, No Drawings

USE OF CROSSLINKED CATIONIC POLYMERS IN SKIN COSMETIC AND DERMATOLOGICAL PREPARATIONS

The present invention relates to the use of crosslinked cationic copolymers in skincare compositions, and to skincare compositions which comprise at least one of these copolymers.

Cationic polymers are frequently used as conditioners in hair cosmetic formulations. They primarily serve to improve the wet combability of hair. Furthermore, cationic polymers prevent the electrostatic charging of hair.

Thus, for example, EP-A-0 246 580 describes the use of uncrosslinked homo- and copolymers of 3-methyl-1-vinylimidazolium chlorides in cosmetic compositions. EP-A-0 544 158 and U.S. Pat. No. 4,859,756 claim the use of uncrosslinked homo- and copolymers of chloride-free, quaternized N-vinylimidazoles in cosmetic preparations. EP-A-0 715 843 discloses the use of uncrosslinked copolymers of a quaternized N-vinylimidazole, N-vinylcaprolactam and N-vinylpyrrolidone, and optionally a further comonomer in cosmetic preparations.

DE-A-28 21 239 (U.S. Pat. No. 4,348,380) describes copolymers of quaternized diallylammonium compounds in hair cosmetic preparations. The polymers are uncrosslinked.

DE-A-31 06 974 describes a hair-treatment composition of the pre-shampooing type, which comprises uncrosslinked homo- and copolymers of quaternized diallylammonium compounds.

U.S. Pat. No. 5,275,809, EP-A-0 522 755, EP-A-0 521 665 and EP-A-0 521 666 disclose copolymers containing dimethyldiallylammonium chloride for use in shampoos. In none of the abovementioned specifications is a crosslinked polymer described.

U.S. Pat. No. 4,806,345 describes crosslinked cationic thickeners for cosmetic formulations comprising quaternized dimethylaminoethyl methacrylate and acrylamide.

WO 93/25595 describes crosslinked cationic copolymers based on quaternized dialkylaminoalkyl acrylates or dialkylaminoalkyl-acrylamides. A proposed application is the use of these crosslinked copolymers as thickeners in cosmetic preparations. A process for the preparation of water-soluble or water-swellable polymers in a W/O emulsion is claimed in EP-A-0 126 528, which comprises polymerizing the water-soluble monomers in the presence of emulsifiers with the addition of a particular dispersion system consisting of alkanols. Cationic comonomers, inter alia, are also used. The oil phases are aliphatic and aromatic hydrocarbons or higher aliphatic esters. The polymers are not intended for cosmetics applications.

DE-A-197 49 618 describes anionic copolymers which are prepared in cosmetic oils in inverse suspension polymerization and used directly in cosmetic formulations.

DE-A-32 09 224 describes the preparation of crosslinked polymers based on N-vinylpyrrolidone and (quaternized) N-vinylimidazole. These polymers are claimed for use as adsorbents and ion exchangers.

Crosslinked, agglomerated vinylimidazole copolymers are mentioned in WO 96/26229 as dye-transfer inhibitors. They are highly crosslinked, water-insoluble and virtually unswellable, and are therefore not suitable as conditioners or gel formers in cosmetic formulations.

U.S. Pat. No. 4,058,491 discloses crosslinked cationic hydrogels comprising N-vinylimidazole or N-vinylpyrrolidone and a quaternized basic acrylate and other comonomers. These gels are proposed for the complexation and controlled relief of anionic active substances.

WO 96/37525 describes the preparation of crosslinked copolymers of, inter alia, N-vinylpyrrolidone and quaternized vinylimidazoles in the presence of polymerization regulators, and their use, in particular, in detergents. The compounds are unsuitable as gel formers.

DE-A-42 13 971 describes copolymers of an unsaturated carboxylic acid, quaternized vinylimidazole and optionally further monomers and a crosslinker. The polymers are proposed as thickeners and dispersants.

The method of thickening by protonation of a water-soluble, crosslinked aminoalkyl(meth)acrylate is described in EP-A-0 624 617 and EP-A-0 027 850.

The use of copolymers comprising an aminoalkyl (meth) acrylate in cosmetics is described in EP-A-0 671 157. However, the polymers mentioned therein are exclusively used for joint use with setting or conditioning polymers.

WO 97/35544 describes the use of crosslinked cationic polymers comprising dialkylaminoalkyl (meth)acrylates or dialkylaminoalkyl (meth)acrylamides in shampoo compositions.

EP-A-0 893 117 describes the use of high molecular weight cationic polymers which comprise bi- or polyfunctional monomers, as conditioning agents in hair cosmetic preparations.

DE-A-197 31 907 describes the use of crosslinked cationic copolymers which comprise N-vinylimidazoles, in hair cosmetic formulations.

It is an object of the present invention then to provide new types of cosmetic compositions which permit improved skin care.

We have found that this object is achieved using the crosslinked cationic copolymers known from DE-A-19 731 764 or EP-A-0 893 117 and DE-A-197 31 907 and proposed therein for the treatment of hair.

The invention firstly relates to the use of crosslinked copolymers obtainable by (i) free-radically initiated copolymerization of a monomer mixture comprising (a) 1 to 99.99% by weight, preferably 2 to 94.98% by weight, particularly preferably 10 to 70% by weight, of at least one monomer chosen from N-vinylimidazoles and diallylamines, optionally in partially or completely quaternized form;

(b) 0 to 98.99% by weight, preferably 5 to 97.98% by weight, particularly preferably 20 to 89.95% by weight, of at least one neutral or basic water-soluble monomer which is different from (a), (c) 0 to 50% by weight, preferably 0 to 40% by weight, particularly preferably 0 to 30% by weight, of at least one unsaturated acid or unsaturated anhydride, (d) 0 to 50% by weight, preferably b to 40% by weight, particularly preferably 0 to 30% by weight, of at least one free-radically copolymerizable monomer which is different from (a), (b) and (c), and (e) 0.01 to 10% by weight, preferably 0.02 to 8% by weight, particularly preferably 0.05 to 5% by weight, of at least one bi- or polyfunctional free-radically copolymerizable monomer, and (ii) subsequent partial or complete quaternization or protonation of the resulting copolymer where monomer (a) is an unquaternized or only partially quaternized monomer, as additive for skin cosmetic and dermatological preparations.

Suitable monomers (a) are the N-vinylimidazole derivatives of the formula (I),

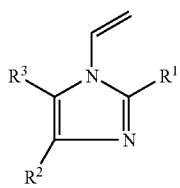

(I)

in which the radicals R¹ to R³ independently of one another are hydrogen, $C_1$-$C_4$-alkyl or phenyl.

Also suitable are diallylamines of the formula (II),

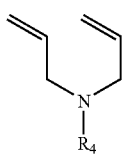

(II)

in which R⁴ is $C_1$-$C_{24}$-alkyl.

The copolymers according to the invention have the advantage over the copolymers used in accordance with the prior art and based on N,N-dialkylaminoalkyl (meth)acrylates or N,N-dialkylaminoalkyl(meth)acrylamide that they do not hydrolyze in aqueous solution and are therefore particularly stable.

Examples of compounds of the formula (I) are given in Table 1 below:

TABLE 1

| R¹ | R² | R³ |
|----|----|----|
| H  | H  | H  |
| Me | H  | H  |
| H  | Me | H  |
| H  | H  | Me |
| Me | Me | H  |
| H  | Me | Me |
| Me | H  | Me |
| Ph | H  | H  |
| H  | Ph | H  |
| H  | H  | Ph |
| Ph | Me | H  |
| Ph | H  | Me |
| Me | Ph | H  |
| H  | Ph | Me |
| H  | Me | Ph |
| Me | H  | Ph |

Me = methyl
Ph = phenyl

Other monomers of the formula (I) which can be used are the ethyl, propyl or butyl analogs of the methyl-substituted 1-vinylimidazoles listed in Table 1.

Examples of compounds of the formula (II) are diallylamines, in which R⁴ is methyl, ethyl, iso- or n-propyl, iso-, n- or tert-butyl, pentyl, hexyl, heptyl, octyl, nonyl or decyl. Examples of longer-chain radicals R⁴ are undecyl, dodecyl, tridecyl, pentadecyl, octadecyl and icosyl.

The monomers (a) can either be used in quaternized form as monomers or be polymerized in nonquaternized form, where, in the latter case, the resulting copolymer is either quaternized or protonated.

Compounds which are suitable for quaternizing the compounds of the formulae (I) and (II) are, for example, alkyl halides having from 1 to 24 carbon atoms in the alkyl group, e.g. methyl chloride, methyl bromide, methyl iodide, ethyl chloride, ethyl bromide, propyl chloride, hexyl chloride, dodecyl chloride, lauryl chloride and benzyl halides, in particular benzyl chloride and benzyl bromide. Other suitable quaternizing agents are Dialkyl sulfates, in particular dimethyl sulfate or diethyl sulfate. The quaternization of the basic monomers of the formulae (I) and (II) can also be carried out using alkylene oxides, such as ethylene oxide or propylene oxide, in the presence of acids.

The quaternization of the monomer or of a polymer using one of said quaternizing agents can be carried out by methods which are generally known.

The quaternization of the copolymer can take place completely or else only partially. The proportion of quaternized monomers (a) in the copolymer can vary over a wide range and is, for example, from about 20 to 100 mol %.

Preferred quaternizing agents are methyl chloride, dimethyl sulfate or diethyl sulfate.

Preferred examples of monomers (a) are 3-methyl-1-vinylimidazolium chloride and methosulfate, and dimethyldiallylammonium chloride.

Particularly preferred monomers (a) are 3-methyl-1-vinylimidazolium chloride and methosulfate.

Compounds which are suitable for the protonation are, for example, mineral acids, such as HCl, $H_2SO_4$, $H_3PO_4$, and monocarboxylic acids, such as, for example, formic acid and acetic acid, dicarboxylic acids and polyfunctional carboxylic acids, such as, for example, oxalic acid and citric acid, and all other proton-donating compounds and substances which are able to protonate the corresponding vinylimidazole or diallylamine. In particular, water-soluble acids are suitable for the protonation.

The polymer can be protonated either after the polymerization or during the formulation of the cosmetic composition, during which, as a rule, a physiologically compatible pH is set.

The term "protonation" means that at least some of the protonatable groups of the polymer, preferably 20 to 100 mol %, are protonated, resulting in an overall cationic charge of the polymer.

Suitable monomers (b) which are different from (a) are N-vinyllactams, such as, for example, N-vinylpiperidone, N-vinylpyrrolidone and N-vinylcaprolactam, N-vinylacetamide, N-methyl-N-vinylacetamide, acrylamide, methacrylamide, N,N-dimethylacrylamide, N-methylolmethacrylamide, N-vinyloxazolidone, N-vinyltriazole, hydroxyalkyl (meth)acrylates, such as for example, hydroxyethyl (meth) acrylate and hydroxypropyl (meth)acrylates, or alkyl ethylene glycol(meth)acrylates having from 1 to 50 ethylene glycol units in the molecule. Also suitable are dialkylaminoalkyl (meth)acrylates and dialkylaminoalkyl(meth)acrylamides, such as, for example, N,N'-dimethylaminoethylmethacrylate or N-[3-(dimethylamino)propyl] methacrylamide.

Preference is given to using N-vinyllactams as monomers (b). Very particular preference is given to N-vinylpyrrolidone.

Compounds which are suitable as monomers (c) are unsaturated carboxylic acids and unsaturated anhydrides, such as, for example, acrylic acid, methacrylic acid, crotonic acid, itaconic acid, maleic acid, fumaric acid or their corresponding anhydrides, unsaturated sulfonic acids, for example acrylamidomethylpropanesulfonic acid, and the salts of the unsaturated acids, such as, for example, the alkali metal or ammonium salts.

Compounds suitable as monomers (d) are $C_1$-$C_{40}$-alkyl esters of (meth)acrylic acid, where the esters are derived from linear, branched-chain or carbocyclic alcohols, e.g. methyl (meth)acrylate, ethyl (meth)acrylate, tert-butyl (meth)acrylate, isobutyl (meth)acrylate, n-butyl (meth)acrylate, stearyl (meth)acrylate, or esters of alkoxylated fatty alcohols, e.g. $C_1$-$C_{40}$-fatty alcohols reacted with ethylene oxide, propylene oxide or butylene oxide, in particular $C_{10}$-$C_{18}$-fatty alcohols reacted with 3 to 150 ethylene oxide units. Also suitable are N-alkyl-substituted acrylamides containing linear, branched-chain or carbocyclic alkyl radicals, such as N-tert-butylacrylamide, N-butylacrylamide, N-octylacrylamide, and N-tert-octylacrylamide.

Also suitable are styrene, and vinyl and allyl esters of $C_1$-$C_{40}$-carboxylic acids which can be linear, branched-chain or carbocyclic, e.g. vinyl acetate, vinyl propionate, vinyl neononanoate, vinyl neoundecanoic acid, vinyl t-butyl benzoate, alkyl vinyl ethers, for example methyl vinyl ether, ethyl vinyl ether, butyl vinyl ether and stearyl vinyl ether.

Acrylamides, such as N-tert-butylacrylamide, N-butylacrylamide, N-octylacrylamide, N-tert-octylacrylamide and N-alkyl-substituted acrylamides containing linear, branched-chain or carbocyclic alkyl radicals, where the alkyl radical can have the meanings given above for $R^4$.

Monomers (e), which have a crosslinking function, are compounds of at least two ethylenically unsaturated, nonconjugated double bonds in the molecule.

Suitable crosslinkers are, for example, acrylic esters, methacrylic esters, allyl ethers or vinyl ethers of at least dihydric alcohols. The OH groups of the parent alcohols can be completely or partially etherified or esterified; however, the crosslinkers contain at least two ethylenically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, mononeopentyl glycol hydroxylpivolate, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and also polyethylene glycols, polypropylene glycols and polytetrahydrofurans each having molecular weights of from 200 to 10,000. As well as the homopolymers of ethylene oxide or propylene oxide, it is also possible to use block copolymers of ethylene oxide or propylene oxide or copolymers which contain incorporated ethylene oxide and propylene oxide groups. Examples of parent alcohols having more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose and mannose. It is of course also possible to use the polyhydric alcohols following reaction with ethylene oxide or propylene oxide and as the corresponding ethoxylates or propoxylates respectively. The polyhydric alcohols can also be first converted into the corresponding glycidyl ethers by reaction with epichlorohydrin.

Other suitable crosslinkers are the vinyl esters or the esters of monohydric, unsaturated alcohols with ethylenically unsaturated $C_3$- to $C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. It is, however, also possible to esterify the monohydric, unsaturated alcohols using polybasic carboxylic acids, for example malonic acid, tartaric acid, trimellitic acid, phthalic acid, terephthalic acid, citric acid or succinic acid.

Other suitable crosslinkers are esters of unsaturated carboxylic acids with the above-described polyhydric alcohols, for example oleic acid, crotonic acid, cinnamic acid or 10-undecanoic acid.

Also suitable as monomers (e) are straight-chain or branched, linear or cyclic, aliphatic or aromatic hydrocarbons which have at least two double bonds, which in the case of aliphatic hydrocarbons must not be conjugated, e.g. divinyl benzene, divinyl toluene, 1,7-octadiene, 1,9-decadiene, 4-vinyl-1-cyclohexene, trivinylcyclohexane or polybutadienes having molecular weights from 200 to 20,000.

Other suitable crosslinkers are acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Also suitable are the amides of allylamine and unsaturated carboxylic acids such as acrylic acid, methacrylic acid or itaconic acid, maleic acid, or at least dibasic carboxylic acids as described above.

Other suitable crosslinkers are triallylamine and triallylmonoalkylammonium salts, e.g. triallylmethylammonium chloride or methylsulfate.

Other suitable crosslinkers are N-vinyl compounds of urea derivatives, at least difunctional amides, cyanurates or urethanes, for example of urea, ethyleneurea, propyleneurea, or tartramide, e.g. N,N'-divinylethyleneurea or N,N'-divinylpropyleneurea.

Further suitable crosslinkers are divinyldioxane, tetrallylsilane or tetravinylsilane.

Preference is given to using crosslinkers which are soluble in the monomer mixture.

Particularly preferred crosslinkers are, for example, pentaerythritol triallyl ether, methylenebisacrylamide, triallylamine and triallylalkylammonium salts, divinylimidazole, N,N'-divinylethyleneurea, reaction products of polyhydric alcohols with acrylic acid or methacrylic acid, methacrylic esters and acrylic esters of polyalkyleneoxides or polyhydric alcohols which have been reacted with ethylene oxide and/or propylene oxide and/or epichlorohydrin.

Very particularly preferred crosslinkers are pentaerythritol triallyl ether, methylenebisacrylamide, N,N'-divinylethyleneurea, triallylamine and acrylic esters of glycol, butanediol, trimethylolpropane or glycerol or acrylic esters of glycol, butanediol, trimethylolpropane or glycerol reacted with ethylene oxide and/or epichlorohydrin.

Each of the monomers (a) to (e) can be used individually or in a mixture with other monomers of the same group.

The polymers are prepared by the processes of free-radically initiated polymerization known per se, e.g. by solution polymerization, emulsion polymerization, suspension polymerization, precipitation polymerization, inverse suspension polymerization, inverse emulsion polymerization or by polymerization in supercritical media, e.g. supercritical carbon dioxide, without being limited thereto.

The polymerization is usually carried out at temperatures of from 20° C. to 150° C. and at atmospheric pressure or under autogenous pressure; the temperature can be kept constant or be increased continuously or discontinuously, e.g. in order to increase the conversion.

Initiators which can be used for the free-radical polymerization are the water-soluble and water-insoluble peroxo and/ or azo compounds customary for this purpose, for example alkali metal or ammonium peroxodisulfates, dibenzoylperoxide, tert-butyl perpivalate, tert-butyl-per-2-ethylhexanoate, di-tert-butyl peroxide, tert-butyl hydroperoxide, azobisisobutyronitrile, azobis(2-amidinopropane) dihydrochloride or 2,2'-azobis(2-methylbutyronitrile). Also suitable are initiator mixtures or redox initiator systems, such as, for example, ascorbic acid/iron(II) sulfate/sodium peroxodisulfate, tert-butyl hydroperoxide/sodium disulfite, tert-butyl hydroperoxide/sodium hydroxymethanesulfinate. The initiators can be used in the customary amounts, for example, 0.05 to 5% by weight, or 0.05 to 0.3 mol %, based on the amount of monomers to be polymerized.

If the copolymers used according to the invention are prepared in inverse suspension polymerization in cosmetic oils, the oil phase chosen according to the invention is a component which has a positive effect on the cosmetic formulation (appearance, feel on the skin). Such components are, for example, native oils, such as sunflower oil, almond oil, avocado oil, wax esters such as jojoba oil, fatty acid isopropyl esters such as isopropyl palmitate, isopropyl myristate, di- and triglycerides of fatty acids, such as, for example, caprylic/capric glycerides. The oil phase proportion in the overall emulsion is 15 to 70% by weight, preferably 20 to 35% by weight.

In order to disperse the water phase in the organic phase, W/O emulsifiers known for this purpose are used. The HLB value of the emulsifiers used is between 4 and 8 [HLB value=hydrophilic/lipophilic balance, cf. W. C. Giffin, J. Soc. Cosmet. Chem. 1, (1950) 311]. Such emulsifiers are, for example, sorbitan monooleate, sorbitan monostearate, glyceryl monostearate, block copolymers of hydroxy fatty acid polyesters and polyoxyethylene. They can be used alone or in combination in overall concentrations of from 2 to 10% by weight, preferably from 2 to 5% by weight, based on the total emulsion.

It is also possible to add emulsifiers with a HLB value of greater than 8 to the emulsion, specifically in concentrations of from 0.25 to 7% by weight, based on the total emulsion. Such emulsifiers are, for example, ethoxylated $C_6$-$C_{12}$-nonylphenols and $C_{12}$-$C_{18}$ fatty alcohols; the degree of ethoxylation is 5 to 20 mol %.

The emulsification of the aqueous phase into the oil phase does not require any special units; the aqueous monomer phase can be emulsified in a standard polymerization vessel by stirring, e.g. with an anchor stirrer. The rate of rotation is between 30 and 400 rpm, depending on the geometry of the tank.

Following the polymerization, water-in-oil emulsions are obtained which have a solids content of from 10 to 40% by weight, preferably from 15 to 35% by weight. To increase the solid content, the emulsions can be partially or completely dewatered by distillation.

The W/O emulsions of crosslinked polymers prepared according to the invention are used as thickeners, preferably in skin cosmetic or dermatological applications. The polymers are not isolated, but used directly in the form of the W/O emulsion. The thickening action of the W/O emulsion takes place immediately after the W/O emulsion has been mixed with a cosmetic O/W emulsion; in order to achieve the optimum effect, no addition of an inversion agent is necessary. Purely aqueous systems can also be thickened. This gives a cream gel.

The molecular weight and the K value of the copolymers used according to the invention can be varied within a wide range in a manner known per se through the choice of polymerization conditions, for example polymerization time, polymerization temperature or initiator concentration, and by the content of crosslinker. The K-values of preferred copolymers are in a range between 30 and 350, preferably 50 and 350.

The K values are measured in accordance with Fikentscher, Cellulosechemie, Vol. 13, pp. 58-64 (1932) at 25° C. 0.1% strength in 0.5 molar sodium chloride solution.

If the degrees of crosslinking are high, the K values for the polymers can not be determined.

The polymers according to the invention can be used in skin cosmetic and dermatological preparations.

For example, the polymers according to the invention are used in cosmetic compositions for cleansing the skin. Such cosmetic cleansers are chosen from bar soaps, such as toilet soaps, curd soaps, transparent soaps, luxury soaps, deodorant soaps, cream soaps, baby soaps, skin-protection soaps, abrasive soaps and syndets, liquid soaps, such as pasty soaps, soft soaps and washing pastes, and liquid wash, shower and bath preparations, such as washing lotions, shower preparations and gels, foam baths, oil baths and scrub preparations.

The polymers according to the invention are preferably used in cosmetic compositions for the care and protection of the skin, in nailcare compositions, and in preparations for decorative cosmetics.

Particular preference is given to the use in skincare compositions, personal hygiene care compositions, footcare compositions, sunscreens, repellants, shaving compositions, depilatories, anti-acne compositions, makeup, mascara, lipsticks, eyeshadows, kohl pencils, eye liners, blushers, powders and eyebrow pencils.

The skincare compositions are, in particular, in the form of W/O or O/W skin creams, day and night creams, eye creams, face creams, antiwrinkle creams, moisturizing creams, bleaching creams, vitamin creams, skin lotions, care lotions and moisturizing lotions.

In the cosmetic and dermatological preparations the polymers according to the invention can develop particular effects. The polymers can, inter alia, contribute to the moisturizing and conditioning of the skin and to improving the feel of the skin. The polymers can also act as thickeners in the formulations. The addition of the polymers according to the invention can, in certain formulations, achieve a considerable improvement in skin tolerability.

The copolymers according to the invention are present in the skin cosmetic and dermatological preparations in an amount of from about 0.001 to 20% by weight, preferably 0.01 to 10% by weight very particularly preferably 0.1 to 5% by weight, based on the total weight of the composition.

Depending on the area of application, the compositions according to the invention can be applied in a form suitable for skincare, such as, for example, as cream, foam, gel, stick, powder, mousse, milk or lotion.

In addition to containing the polymers according to the invention and suitable solvents, the skin cosmetic preparations can also comprise additives customary in cosmetics, such as emulsifiers, preservatives, perfume oils, cosmetic active ingredients, such as phytantriol, Vitamin A, E and C, retinol, bisabolol, panthenol, sunscreens, bleaching agents, colorants, tinting agents, tanning agents (e.g. dihydroxyacetone), collagen, protein hydrolysates, stabilizers, pH regulators, dyes, salts, thickeners, gel formers, bodying agents, silicones, moisturizers, refatting agents and other customary additives.

Suitable solvents which can be mentioned in particular are water and lower monoalcohols or polyols having from 1 to 6 carbon atoms or mixtures thereof; preferred monoalcohols or polyols are ethanol, isopropanol, propylene glycol, glycerol and sorbitol.

Other customary additives which may be present are fatty substances, such as mineral and synthetic oils, such as, for example, paraffins, silicone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglyerides of $C_6$-$C_{30}$-fatty acids, wax esters, such as, for example, jojoba oil, fatty alcohols, vaseline, hydrogenated lanolin and acetylated lanolin. It is of course also possible to use mixtures thereof.

Customary thickeners in formulations of this type are crosslinked polyacrylic acids and derivatives thereof, polysaccharides such as xanthan gum, agar agar, alginates or tyloses, carboxymethylcellulose or hydroxycarboxymethylcellulose, fatty alcohols, monoglycerides and fatty acids, polyvinyl alcohol and polyvinylpyrrolidone.

The polymers according to the invention can also be mixed with traditional polymers if specific properties are to be set.

Suitable traditional polymers are, for example, anionic, cationic, amphoteric and neutral polymers.

Examples of anionic polymers are homo- and copolymers of acrylic acid and methacrylic acid or salts thereof, copolymers of acrylic acid and acrylamide and salts thereof; sodium salts of polyhydroxycarboxylic acids, water-soluble or water-dispersible polyesters, polyurethanes and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luvimer® MAE), copolymers of N-tert-butylacrylamide, ethyl acrylate, acrylic acid (Ultrahold® 8, strong), copolymers of vinyl acetate, crotonic acid and optionally further vinyl esters (e.g. Luviset® grades), maleic anhyride copolymers, optionally reacted with alcohols, anionic polysiloxanes, e.g. carboxyfunctional ones, copolymers of vinylpyrrolidone, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of (meth)acrylic acid, $C_4$-$C_{30}$-alkylvinyl esters, $C_4$-$C_{30}$-alkyl vinyl ethers and hyaluronic acid.

Further suitable polymers are cationic polymers with the INCI name polyquaternium, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethylsulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and 10), acrylamide copolymers (polyquaternium-7) and chitosan.

Also suitable as further polymers are neutral polymers, such as polyvinylpyrrolidones, copolymers of N-vinylpyrrolidone and vinyl acetate and/or vinyl propionate, polysiloxanes, polyvinylcaprolactam and copolymers containing N-vinylpyrrolidone, polyethylenimines and salts thereof, polyvinylamines and salts thereof, cellulose derivatives, polyaspartic acid salts and derivatives.

To set certain properties, the preparations can additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The copolymers according to the invention are used in cosmetic or dermatological preparations, the preparation of which is carried out in accordance with the customary principles familiar to the person skilled in the art.

Such formulations are advantageously in the form of emulsions, preferably as water-in-oil (W/O) or oil-in-water (O/W) emulsions. According to the invention, it is, however, also possible and in some cases advantageous to choose other types of formulation, for example hydrodispersions, gels, oils, oleogels, multiple emulsions, for example in the form of W/O/W or O/W/O emulsions, anhydrous ointments or ointment bases etc.

The emulsions which can be used according to the invention are prepared by known methods.

In addition to the copolymer according to the invention, the emulsions comprise customary constituents, such as fatty alcohols, fatty acid esters and, in particular, fatty acid triglycerides, fatty acids, lanolin and derivatives thereof, natural or synthetic oils or waxes and emulsifiers in the presence of water.

The choice of emulsion-type-specific additives and the preparation of suitable emulsions is described, for example, in Schrader, Grundlagen und Rezepturen der Kosmetika [Cosmetic bases and formulations], Hüthig Buch Verlag, Heidelberg, 2nd Edition, 1989, third part, to which reference is expressly made here.

Thus, a skin cream which can be used according to the invention can, for example, be in the form of a W/O emulsion. An emulsion of this type comprises an aqueous phase which is emulsified in an oil or fatty phase using a suitable emulsifier system.

The concentration of the emulsifier system in this type of emulsion is about 4 to 35% by weight, based on the total weight of the emulsion; the fatty phase constitutes about 20 to 60% by weight, and the aqueous phases about 20 to 70% by weight, in each case based on the total weight of the emulsion. The emulsifiers are those which are customarily used in this type of emulsion. They are, for example, chosen from: $C_{12}$-$C_{18}$ sorbitan fatty acid esters; esters of hydroxystearic acid and $C_{12}$-$C_{30}$ fatty alcohols; mono- and diesters of $C_{12}$-$C_{18}$ fatty acids and glycerol or polyglycerol; condensates of ethylene oxide and propylene glycols; oxypropylenated/oxyethylenated $C_{12}$-$C_{20}$ fatty alcohols; polycyclic alcohols, such as sterols; aliphatic alcohols having a high molecular weight, such as lanolin; mixtures of oxypropylenated/polyglycerolated alcohols and magnesium isostearate; succinyl esters of polyoxyethylenated or polyoxypropylenated fatty alcohols; and mixtures of magnesium, calcium, lithium, zinc or aluminum lanolate and hydrogenated lanolin or lanolin alcohol.

Suitable fatty components which can be present in the fatty phase of the emulsions include hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, Karité oil, Hoplostethus oil, mineral oils whose distillation start point under atmospheric pressure is at about 250° C. and whose distillation end point is at 410° C., such as, for example, vaseline oil; esters of saturated or unsaturated fatty acids, such as alkyl myristates, e.g., isopropyl, butyl or cetyl myristate, hexadecyl stearate, ethyl or isopropyl palmitate, octanoic or decanoic triglycerides and cetyl ricinoleate.

The fatty phase can also comprise silicone oils which are soluble in other oils, such as dimethylpolysiloxane, methylphenylpolysiloxane and the silicone glycol copolymer, fatty acids and fatty alcohols.

In order to favor the retention of oils, it is also possible to use waxes, such as, for example, carnauba wax, candellila wax, beeswax, microcrystalline wax, ozokerite wax and Ca, Mg and Al oleates, myristates, linoleates and stearates.

These water-in-oil emulsions are generally prepared by adding the fatty phase and the emulsifier to the batch container. These are then heated at a temperature of from 70 to 75° C., then the oil-soluble ingredients are added and, with stirring, water is added which has been heated beforehand to the same temperature and in which the water-soluble ingredients have been dissolved beforehand; the mixture is stirred until an emulsion of the desired fineness is obtained, which is then left to cool to room temperature, if necessary with gentle stirring.

A care emulsion according to the invention can also be in the form of an O/W emulsion. An emulsion of this type usually comprises an oil phase, emulsifiers which stabilize the oil phase in the water phase, and an aqueous phase, which is usually in thickened form.

The aqueous phase of the O/W emulsion of the preparations according to the invention optionally comprises alcohols, diols or polyols and ethers thereof, preferably ethanol, isopropanol, propylene glycol, glycerol, ethylene glycol monoethyl ether;

customary thickeners or gel formers, such as, for example, crosslinked polyacrylic acids and derivatives thereof, polysaccharides, such as xantham gum or alginates, carboxymethylcellulose of hydroxycarboxymethylcellulose, fatty alcohols, polyvinyl alcohol and polyvinylpyrrolidone.

The oil phase comprises oil components which are customary in cosmetics, such as, for example:

esters of saturated and/or unsaturated, branched and/or unbranched $C_3$-$C_{30}$-alkane carboxylic acids and saturated and/or unsaturated, branched and/or unbranched $C_3$-$C_{30}$-alcohols, of aromatic carboxylic acids and saturated and/or unsaturated, branched and/or unbranched $C_3$-$C_{30}$-alcohols, for example, isopropylmyristate, isopropyl stearate, hexyldecylstearate, oleyloleate; and also synthetic, semisynthetic and natural mixtures of such esters, such as jojoba oil;

branched and/or unbranched hydrocarbons and hydrocarbon waxes;

silicone oils, such as cyclomethicone, dimethylpolysiloxane, diethylpolysiloxane, octamethylcyclotetrasiloxne and mixtures thereof;

dialkyl ethers;

mineral oils and mineral waxes;

triglycerides of saturated and/or unsaturated, branched and/or unbranched $C_8$-$C_{24}$-alkanecarboxylic acids; they can be chosen from synthetic, semisynthetic or natural oils, such as olive oil, palm oil, almond oil or mixtures.

Suitable emulsifiers are, preferably, O/W emulsifiers, such as polyglycerol esters, sorbitan esters or partially esterified glycerides.

The preparation can be carried out by melting the oil phase at about 80° C.; the water-soluble constituents are dissolved in hot water, then slowly and with stirring added to the oil phase; the mixture is then homogenized and stirred until cold.

The copolymers according to the invention are also suitable for use in washing and shower gel formulations, and also bath preparations.

In addition to the polymers according to the invention, such formulations usually comprise anionic surfactants as base surfactants, and amphoteric and nonionic surfactants as cosurfactants, and also lipids, perfume oils, dyes, organic acids, preservatives and antioxidants, and thickeners/gel formers, skin conditioning agents and moisturizers.

In the wash, shower and bath preparations it is possible to use all anionic, neutral, amphoteric or cationic surfactants which are customarily used in body-cleansing compositions.

The formulations comprise from 2 to 50% by weight of surfactants, preferably from 5 to 40% by weight, particularly preferably from 8 to 30% by weight.

Suitable anionic surfactants are, for example, alkyl sulfates, alkylether sulfates, alkylsulfonates, alkylaryl sulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

Suitable examples of sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzene sulfonate, triethanolamine dodecylbenzenesulfonate.

Suitable amphoteric surfactants are, for example, alkylbetaines, alkylamidopropylbetaines, alkylsulfobetaines, alkylglycinates, alkylcarboxyglycinates, alkylamphoacetates or -propionates, alkylamphodiacetates or -dipropionates.

For example, cocodimethylsulfopropylbetaine, lauryl betaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain which can be linear or branched, with ethylene oxide and/or propylene oxide. The amount of alkylene oxide is about 6 to 60 moles per mole of alcohol. Also suitable are alkylamine oxides, mono- and dialkylalkanolamides, fatty acid esters of polyethyleneglycols, ethoxylated fatty acids amides, alkyl polyglycosides or sorbitan ether esters.

In addition, the wash, shower and bath preparations can comprise customary cationic surfactants, such as, for example, quaternary ammonium compounds, for example cetyltrimethylammonium chloride.

In addition, it is also possible to use further customary cationic polymers, such as, for example, copolymers of acrylamide and dimethyldiallylammonium chloride (polyquaternium-7), cationic cellulose derivatives (polyquaternium-4, -10), guar hydroxypropyltrimethylammonium chloride (INCI: Hydroxypropyl Guar Hydroxypropyltrimonium Chloride), copolymers of N-vinylpyrrolidone and quaternized N-vinylimidazole (polyquaternium-16, -44, -46), copolymers of N-vinypyrrolidone/dimethylaminoethyl methacrylate, quaternized with diethylsulfate (polyquaternium-11) and others.

Furthermore, the wash and shower gel formulations and bath preparations can comprise thickeners, such as, for example, sodium chloride, PEG-55, propylene glycol oleates, PEG-120 methyl glucose dioleates and others and also preservatives, further active ingredients and auxiliaries and water.

A PREPARATION OF THE POLYMERS

Preparation Example 1

A stirred apparatus was charged with 400 g of water and 46 g of dimethyldiallylammonium chloride solution (65% strength). 10% of Feed 1, consisting of 270 g of N-vinylpyrrolidone and 0.6 g of N,N'-divinylethyleneurea, were added to this initial charge. The mixture was heated to 60° C. with stirring in a stream of nitrogen, and Feed 1 was metered in over the course of 3 hours, and Feed 2 consisting of 0.9 g of 2,2'-azobis(2-amidinopropane)-dihydrochloride in 100 g of water, was metered in over the course of 4 hours. After 3 hours, the mixture was diluted with 700 g of water and stirred for a further hour. Then, 1.5 g of 2,2'-azobis(2-amidinopropane)dihydrochloride in 30 g of water were added and the mixture was stirred for a further 2 hours at 60° C. This gave a colorless high-viscosity polymer solution with a solids content of 20.9% and a K value of 80.3.

Preparation Example 2

A stirred apparatus was charged with 300 g of Feed 1, consisting of 200 g of N-vinylpyrrolidone, 77 g of dimethyl-diallylammonium chloride solution (65% strength), 1.13 g of N,N'-divinyl-ethyleneurea and 440 g of water, and the mixture was heated to 60° C. with stirring in a stream of nitrogen. The remainder of Feed 1 was metered in over 2 hours and Feed 2, consisting of 0.75 g of 2,2'-azobis(2-amidinopropane)dihydrochloride in 100 g of water, was metered in over 4 hours. When the addition of Feed 1 was complete, the reaction mixture was diluted with 1620 g of water. When the addition of Feed 2 was complete, the mixture was stirred for a further hour at 60° C., then 1.25 g of 2,2'-azobis(2-amidinopropane)dihydrochloride in 65 g of water were added and the mixture was stirred for a further hour. This gave a colorless high-viscosity polymer solution with a solids content of 10.2% and a K value of 80.

Preparation Example 3

A stirred apparatus was charged with 130 g of water and 48 g of 3-methyl-1-vinylimidazolium chloride, and the mixture was heated to 60° C. with stirring in a stream of nitrogen. Then, Feed 1, consisting of 192 g of N-vinylpyrrolidone, 0.48 g of N,N'-divinylethyleneurea and 450 g of water, was metered in over 3 hours, and Feed 2, consisting of 1.44 g of 2,2'-azobis(2-amidinopropane)dihydrochloride in 80 g of water, was metered in over 4 hours. The mixture was then stirred for a further hour at 60° C. In order to keep the mixture stirrable, it was diluted with a total of 2100 g of water as required. This gave a colorless high-viscosity polymer solution with a solids content of 8.2% and a K value of 105.

Preparation Example 4

716 g of water were charged to a stirred apparatus and, with stirring and in a stream of nitrogen, heated to 60° C. Then, Feed 1, consisting of 180 g N-vinylpyrrolidone, 20 g of 3-methyl-1-vinylimidazolium methylsulfate, 0.32 g of N,N'-divinylethyleneurea and 25 g of water, was metered in over 2 hours, and Feed 2, consisting of 0.6 g of 2,2'-azobis-(2-amidinopropane)dihydrochloride in 60 g of water, was metered in over 3 hours. When the addition of Feed 1 was complete, the reaction mixture was diluted with 1000 g of water. Following the addition of Feed 2, the mixture was stirred for a further 3 hours at 70° C. This gives a colorless high-viscosity polymer solution with a solids content of 11.0% and a K value of 86.

Preparation Example 5

440 g of water were charged to a stirred apparatus and, with stirring and in a stream of nitrogen, heated to 60° C. Then, Feed 1, consisting of 180 g of N-vinylpyrrolidone, 20 g of 3-methyl-1-vinylimidazolium methylsulfate, 0.30 g of N,N'-divinylethylene-urea and 25 g of water, was metered in over 2 hours, and Feed 2, consisting of 0.6 g of 2,2'-azobis(2-amidinopropane)dihydro-chloride in 60 g of water, was metered in over 3 hours. Following the addition of Feed 2, the mixture was stirred for a further 3 hours at 70° C. In order to keep the reaction mixture stirrable, it was diluted with a total of 1275 g of water as required. This gave a colorless high-viscosity polymer solution with a solids content of 11.3% and a K value of 105.

Preparation Example 6

650 g of water were charged to a stirred apparatus and, with stirring and in a stream of nitrogen, heated to 60° C. Then, Feed 1, consisting of 225 g of N-vinylpyrrolidone, 25 g of 2,3-dimethyl-1-vinylimidazolium methylsulfate, 0.25 g of N,N'-divinylethyleneurea and 580 g of water, was metered in over 3 hours, and Feed 2, consisting of 0.7 g of 2,2'-azobis-(2-amidinopropane)dihydrochloride in 100 g of water, was metered in over 4 hours. When the addition of Feed 1 was complete, the reaction mixture was diluted with 835 g of water. Following the addition of Feed 2, the mixture was stirred for a further hour, and 1.25 g of 2,2'-azobis(2-amidinopropane)dihydrochloride in 77 g of water were then added. The mixture was then stirred for a further 2 hours at 70° C. This gave a colorless high-viscosity polymer solution with a solids content of 10.4% and a K value of 106.

Preparation Example 7

650 g of water were charged to a stirred apparatus and, with stirring and in a stream of nitrogen, heated to 60° C. Then, Feed 1, consisting of 225 g of N-vinypyrrolidone, 25 g of 2,3-dimethyl-1-vinylimidazolium methylsulfate, 0.375 g of N,N'-divinylethyleneurea and 580 g of water, was metered in over 3 hours, and Feed 2, consisting of 0.7 g of 2,2'-azobis-(2-amidinopropane)dihydrochloride in 100 g of water, was metered in over 4 hours. After the addition of Feed 1 was complete, the reaction mixture was diluted with 1135 g of water. Following the addition of Feed 2, the mixture was stirred for a further hour, and 1.25 g of 2,2'-azobis(2-amidinopropane)dihydrochloride in 77 g of water were then added. The mixture was then stirred for a further 2 hours at 70° C. This gave a colorless high-viscosity polymer solution with a solid content of 9.2% and a K value of 92.

Preparation Example 8

800 g of cyclohexane, 5 g of sorbitan monooleate, 5 g of Hypermer B246 (Hypermer B246: polymeric surfactant from ICI) and 1 g of 2,2'-azobis(2,4-dimethylvaleronitrile) were heated to 65° C. in a reaction vessel with nitrogen blanketing. The feed, consisting of 100 g of 3-methyl-1-vinylimidazolium methylsulfate, 100 g of N-vinylpyrrolidone, 100 g of water and 0.25 g of tripropylene glycol diacrylate, was metered in over the course of 20 minutes. The mixture was then stirred for 6 hours at 65° C. 200 g of cyclohexane were then added, and the water was distilled off azeotropically, and the polymer was filtered off and dried. The K value of an aqueous solution of the polymer was 114.

Preparation Example 9

900 g of ethyl acetate were charged to a stirred apparatus and, with stirring and in a stream of nitrogen, heated to 77° C. Then, Feed 1, consisting of 270 g of N-vinylpyrrolidone, 30 g of 1-vinylimidazole and 0.3 g of N,N'-divinylethyleneurea, was metered in over 3 hours, and Feed 2, consisting of 3 g of 2,2'-azobis(2-methylbutyronitrile) in 80 g of ethyl acetate, was metered in over 4 hours. The mixture was then stirred for a further 2 hours and cooled to room temperature, and 36 g of dimethyl sulfate were added thereto. The mixture is then stirred for half an hour at room temperature and for a further 2 hours at 70° C. The resulting powder was filtered off and dried. The K value of an aqueous solution of the polymer was 125.

Preparation Example 10

440 g of water were charged to a stirred apparatus and, with stirring and in a stream of nitrogen, heated to 60° C. Then, Feed 1, consisting of 144 g of N-vinylpyrrolidone, 16 g of 3-methyl-1-vinylimidazolium methylsulfate, 1.4 g of tetraethylene glycol diacrylate and 100 g of water, was metered in over 2 hours, and Feed 2, consisting of 0.8 g of 2,2'-azobis(2-amidino-propane)dihydrochloride in 50 g of water, was metered in over 3 hours. Following the addition of Feed 2, the mixture was stirred for a further 3 hours at 70° C. In order to keep the reaction mixture stirrable, it was diluted with a total of 1200 g of water as required. This gave a colorless high-viscosity polymer solution with a solids content of 8.5% and a K value of 95.

Preparation Example 11

550 g of water were charged to a stirred apparatus and, with stirring and in a stream of nitrogen, heated to 60° C. Then, Feed 1, consisting of 102 g of N-vinylpyrrolidone, 26 g of 3-methyl-1-vinylimidazolium methylsulfate, 0.8 g of triallylamine and 100 g of water, was metered in over 2 hours. Feed 2, consisting of 0.6 g of 2,2'-azobis(2-amidinopropane)dihydrochloride in 50 g of water, was added to the reaction mixture over 3 hours. Following the addition of Feed 2, the mixture was stirred for a further 3 hours at 70° C. In order to keep the reaction mixture stirrable, it was diluted with a total of 1000 g of water as required. This gave a slightly yellowish high-viscosity polymer solution with a solids content of 7.0% and a K value of 102.

Preparation Example 12

Preparation Example 11 was repeated, but using 2.2 g of pentaerythritol triallyl ether instead of triallylamine. This gave a slightly yellowish high-viscosity polymer solution with a K value of 95.

Preparation Example 13

440 g of water were charged to a stirred apparatus and, with stirring and in a stream of nitrogen, heated to 60° C. Then, Feed 1, consisting of 150 g of N-vinylpyrrolidone, 8 g of 3-methyl-1-vinylimidazolium methylsulfate, 0.6 g of triallylamine and 100 g of water, was metered in over 2 hours, and Feed 2, consisting of 0.8 g of 2,2'-azobis(2-amidinopropane) dihydrochloride in 50 g of water, was metered in over 3 hours. Following the addition of Feed 2, the mixture was stirred for a further 3 hours at 70° C. In order to keep the reaction mixture stirrable, it was diluted with a total of 1200 g of water as required. This gave a colorless high-viscosity polymer solution with a solids content of 8.1% and K value of 98.

Preparation Example 14

800 g of cyclohexane, 5 g of sorbitan monooleate and 5 g of Hypermer B246 (Hypermer B246: polymeric surfactant from ICI) were charged to a reaction vessel with nitrogen blanketing and heated to 60° C. Feed 1, consisting of 60 g of 3-methyl-1-vinylimidazolium methylsulfate, 140 g of N-vinylpyrrolidone, 150 g of water and 1.0 g of triallylamine, and Feed 2, consisting of 0.6 g of 2,2'-azobis(2-amidinopropane)dihydrochloride in 50 g of water, were metered in over the course of 1 hour. The mixture was then stirred for a further 6 hours at 60° C. 200 g of cyclohexane were then added and the water was distilled off azeotropically, and the polymer was filtered off and dried.

Preparation Example 15

800 g of cyclohexane, 5 g of sorbitan monooleate and 5 g of Hypermer B246 (Hypermer B246; polymeric surfactant from ICI) were charged to a reaction vessel with nitrogen blanketing and heated to 60° C. Feed 1, consisting of 20 g of 3-methyl-1-vinylimidazolium methylsulfate, 180 g of N-vinylpyrrolidone, 150 g of water and 0.5 g of triallylamine, was metered in over the course of 1 hour, and Feed 2, consisting of 1.2 g of 2,2'-azobis(2-amidino-propane)dihydrochloride in 70 g of water, was metered in over the course of 4 hours. The mixture was then stirred for a further 3 hours at 60° C. 200 g of cyclohexane were then added, and the water was distilled off azeotropically, and the polymer was filtered off and dried.

Preparation Example 16

400 g of water, 100 g of N-vinylpyrrolidone, 11 g of 3-methyl-1-vinylimidazolium methylsulfate and 0.4 g of triallylamine were charged to a stirred apparatus and, with stirring and in a stream of nitrogen, heated to 60° C. Then, Feed 1, consisting of 0.6 g of 2,2'-azobis(2-amidinopropane)dihydrochloride in 50 g of water, was added to the reaction mixture over 3 hours, and the mixture was diluted with 1000 g of water. The mixture was then stirred for a further 3 hours at 80° C. This gave a colorless, high-viscosity polymer solution with a solids content of 7.6% and K value of 110.

Preparation Example 17

In a reaction vessel 500 g of cyclohexane, 12 g of sorbitan monooleate, 6 g of Hypermer B246 (Hypermer B246: polymeric surfactant from ICI) and an aqueous phase comprising 150 g of 3-methyl-1-vinylimidazolium methylsulfate, 150 g of vinylpyrrolidone, 0.75 g of 2,2'-azobis(2-amidinopropane) dihydrochloride, 360 g of water and 0.6 g of divinylethyleneurea were polymerized for 6 h at 70° C. The water was then distilled off azeotropically, and the polymer was filtered off and dried.

Preparation Example 18

In a reaction vessel, 200 g of Mygliol (caprylic/capric triglycerides from Huls AG), 12 g of sorbitan monooleate, 6 g of Hypermer B246 (ICI) and an aqueous phase comprising 333 g of vinylimidazolium methylsulfate, 150 g of vinylpyrrolidone, 0.75 g of 2,2'-azobis(2-amidinopropane) dihydrochloride, 186 g of water and 0.6 g of divinylethyleneurea were polymerized for 6 h at 70° C.

Preparation Example 19

500 g of water were charged to a stirred apparatus and heated to 60° C. Then, Feed 1, consisting of 125 g of vinylimidazole, 48 g of acrylic acid, 42 g of NaOH (50% strength aqueous solution), 0.8 g of triallylamine and 500 g of water, and Feed 2, consisting of 1.25 g of 2,2'-azobis(2-amidinopropane)dihydrochloride and 200 g of water, were added over 4 h. The internal temperature was then increased to 70° C., 1.25 g of 2,2'-azobis(2-amidinopropane) dihydrochloride in 78 g of water were added over the course of 1 h, and then the mixture was stirred for a further 1 h at 70° C. In order to keep the reaction mixture stirrable, it was diluted with a total of 1200 g of water as required. This gave a slightly yellowish polymer solution with a solids content of 7.8% and a K value of 110.

Preparation Example 20

Preparation Example 19 was repeated, but using 125 g of 3-methyl-1-vinylimidazolium methylsulfate instead of 125 g of 1-vinylimidazole. This gave a slightly yellowish polymer solution with a solids content of 7.8% and a K value of 105.

B APPLICATION EXAMPLES

Application Example 1

Skin Cream

Firstly, a water/oil cream emulsion (skin cream A) was prepared in accordance with the following recipe:

| | Additive | % by weight |
| --- | --- | --- |
| Cremophor A 6 | Ceteareth-6 and stearyl alcohol | 2.0 |
| Chremophor A 25 | Ceteareth-25 | 2.0 |
| Lanette O | cetearyl alcohol | 2.0 |
| Imwitor 960 K | glyceryl stearate SE | 3.0 |
| Paraffin oil | | 5.0 |
| Jojoba oil | | 4.0 |
| Luvitol EHO | cetearyl octanoate | 3.0 |
| ABIL 350 | dimethicone | 1.0 |
| Amerchol L 101 | mineral oil and lanolin alcohol | 3.0 |
| Veegum Ultra | magnesium aluminum silicate | 0.5 |
| 1,2-Propylene glycol | propylene glycol | 5.0 |
| Abiol | imidazolindinylurea | 0.3 |
| Phenoxyethanol | | 0.5 |
| D-Panthenol USP | | 1.0 |
| Polymer (Preparation Example 11) | | 0.5 |
| Water | | ad 100 |

Two comparison creams were prepared in the same way:

Skin cream B (without polymer additive)

Skin cream C (polymer according to the invention replaced by the same amount of an uncrosslinked copolymer of 30 mol % of vinylimidazolium chloride and 70 mol % of N-vinylpyrrolidone)

Using these skin creams A, B and C, the following comparative tests 1 and 2 were carried out to assess the feel on the skin.

100 µl of the emulsion were distributed uniformly on the back of the hand, and the feel on the skin was tested subjectively after a contact time of 30 minutes. In each case two emulsions were compared with one another (right/left hand). Each of the tests was carried out by ten subjects.

Scale of Grades:

2 (markedly softer than comparison cream)

1 (somewhat softer than comparison cream)

0 (equal)

−1 (somewhat rougher than comparison cream)

−2 (markedly more rough than comparison cream

Result of comparison test 1 (comparison of skin cream A and comparison cream B):

| Grade | No. of subjects |
| --- | --- |
| 2 | 5 |
| 1 | 4 |
| 0 | 1 |
| −1 | — |
| −2 | — |

Result of comparison test 2 (comparison of skin cream A and comparison cream C):

| Grade | No. of subjects |
| --- | --- |
| 2 | 3 |
| 1 | 5 |
| 0 | 2 |
| −1 | — |
| −2 | — |

Application Example 2

Shower Gel

A shower gel formulation according to the invention (shower gel A) was firstly prepared in accordance with the following recipe:

| | Additives | % by weight |
| --- | --- | --- |
| Texapon NSO | sodium laureth sulfate | 40.0 |
| Tego Betaine L7 | cocamidopropylbetaine | 5.0 |
| Plantacare 2000 | decylglucoside | 5.0 |
| Perfume | | 0.2 |
| Polymer as in Preparation Example 11 | | 0.2 |
| Euxyl K 100 | benzyl alcohol, methyl-chlorisothiazolinone, methyl-isothiazolinone | 0.1 |
| D-Panthenol USP | | 0.5 |
| Citric acid (pH 6-7) | | q.s. |
| NaCl | | 2.0 |
| Water | | ad 100 |

Three comparison shower gels were prepared in the same manner:

Shower gel B: (copolymer according to the invention replaced by the same amount of the uncrosslinked polymer polyquaternium-16)

Shower gel C: (copolymer according to the invention replaced by the same amount of cationically modified hydroxyethylcellulose)

Shower gel D: (without polymer addition)

Using the shower gels A, B, C and D, the following comparison test 3 was carried out to determine the foam creaminess:

2.0 g of each of the abovementioned formulations was placed into the palm of the left hand, lathered using tap water and, after rubbing between both hands for 1 minute, the feel of the foam in the palms of the hands was assessed:

Grade 1: very creamy

Grade 2: creamy

Grade 3: flat/lacking substance

Result of Comparison test 3 (mean value of the rating by 10 subjects):

| Shower gel | Mean value from 10 subjects |
|---|---|
| A | 1.3 |
| B | 2.8 |
| C | 2.1 |
| D | 2.8 |

Application Example 3

Moisturizing Formulation

Formulation A

| | Additive | | % by weight |
|---|---|---|---|
| a) | Cremophor A6 | Ceteareth-6 and stearyl alcohol | 2.0 |
| | Cremophor A25 | Ceteareth-25 | 2.0 |
| | Paraffin oil (viscous) | | 10 |
| | Lannette O | cetearyl alcohol | 2.0 |
| | Stearic acid | | 3.0 |
| | Nip-Nip | methylparaben/propylparaben 70:30 | 0.5 |
| | Abiol | imidazolidinylurea | 0.5 |
| b) | Polymer (Preparation Example 8) | | 3.0 |
| | Water | | ad 100.0 |

The two phases were heated to 80° C., phase a) was fed into b) and the mixture was homogenized and stirred until cold and then adjusted to pH 6 with 10% strength aqueous NaOH solution.

In the same manner, a comparison cream (formulation B) without polymer additive was prepared.

Using the formulations A and B, a test was carried out on eight subjects. For this, each of the formulations was applied in an amount of 2 mg/cm$^2$ to the forearm of the subjects. After 30 min the moisture content of the skin was determined using a corneometer CM 825 (Khazaka & Courage). After applying formulation A a mean value of 45 corneometer units was measured, and for formulation B a mean value of 35.

Application Example 4

O/W Cream for Moisturizing the Skin

| Additive | % by weight |
|---|---|
| Glycerol monostearate | 2.0 |
| Cetyl alcohol | 3.0 |
| Paraffin oil, subliquidum | 15.0 |
| Vaseline | 3.0 |
| Caprylic/capric triglyceride | 4.0 |
| Octyldodecanol | 2.0 |
| Hydrogenated coconut fat | 2.0 |
| Cetyl phosphate | 0.4 |
| Polymer (Preparation Example 6) | 3.0 |
| Glycerol | 3.0 |
| Sodium hydroxide | q.s. |
| Perfume oil | q.s. |
| Preservative | q.s. |
| Water | ad 100 |

Application Example 5

O/W Lotion

| Additive | % by weight |
|---|---|
| Stearic acid | 1.5 |
| Sorbitan monostearate | 1.0 |
| Sorbitan monooleate | 1.0 |
| Paraffin oil, subliquidum | 7.0 |
| Cetyl alcohol | 1.0 |
| Polydimethylsiloxane | 1.5 |
| Glycerol | 3.0 |
| Polymer (Preparation Example 17) | 0.5 |
| Perfume oil | q.s. |
| Preservative | q.s. |
| Water | ad 100 |

Application Example 6

W/O Cream

| Additive | % by weight |
|---|---|
| PEG-7 hydrogenated castor oil | 4.0 |
| Wool wax alcohol | 1.5 |
| Beeswax | 3.0 |
| Triglyceride, liquid | 5.0 |
| Vaseline | 9.0 |
| Ozokerite | 4.0 |
| Paraffin oil, subliquidum | 4.0 |
| Glycerol | 2.0 |
| Polymer (Preparation Example 4) | 2.0 |
| Magnesiumsulfate*7H$_2$O | 0.7 |
| Perfume oil | q.s. |
| Preservative | q.s. |
| Water | ad 100 |

Application Example 7

Hydrogel for Skincare

| Additive | % by weight |
| --- | --- |
| Polymer (Preparation Example 17) | 3.0 |
| Sorbitol | 2.0 |
| Glycerol | 3.0 |
| Polyethylene glycol 400 | 5.0 |
| Ethanol | 1.0 |
| Perfume oil | q.s. |
| Preservative | q.s. |
| Water | ad 100 |

Application Example 8

Hydrodispersion Gel

| Additive | % by weight |
| --- | --- |
| Polymer (Preparation Example 17) | 3.0 |
| Sorbitol | 2.0 |
| Glycerol | 3.0 |
| Polyethylene glycol 400 | 5.0 |
| Triglyceride, liquid | 2.0 |
| Ethanol | 1.0 |
| Perfume oil | q.s. |
| Preservative | q.s. |
| Water | ad 100 |

Application Example 9

Liquid Soap

| Additive | % by weight |
| --- | --- |
| Coconut fatty acid, potassium salt | 15 |
| Potassium oleate | 3 |
| Glycerol | 5 |
| Polymer (Preparation Example 14) | 2 |
| Glycerol stearate | 1 |
| Ethylene glycol distearate | 2 |
| Specific additives, complexing agents, fragrances, | q.s. |
| Water | ad 100 |

Application Example 10

Bodycare Cream

| Additive | | % by weight |
| --- | --- | --- |
| Cremophor A6 | Ceteareth-6 and stearyl alcohol | 2.0% |
| Cremophor A 25 | Ceteareth-25 | 2.0% |
| Grape (*Vitis vinifera*) seed oil | | 6.0% |
| Glyceryl stearate SE | | 3.0% |
| Cetearyl alcohol | | 2.0% |
| Dimethicon | | 0.5% |
| Luvitol EHO | Cetearyloctanoate | 8.0% |
| Oxynex 2004 | propylene glycol, BHT, ascorbyl palmitate, glyceryl stearate, citric acid | 0.1% |
| Preservative | | q.s. |
| 1,2-Propylene glycol USP | | 3.0% |
| Glycerol | | 2.0% |
| EDTA BD | | 0.1% |
| D-Panthenol USP | | 1.0% |
| Water | | ad 100 |
| Polymer (Preparation Example 11) | | 1.5% |
| Tocopheryl acetate | | 0.5% |

The formulation had a pH of 6.8. The viscosity (Brookfield RVT, 23° C.) was 32.000 mPas.

We claim:

1. In a skin cosmetic or dermatological preparation selected from cosmetic compositions for cleansing the skin, cosmetic compositions for the care and protection of the skin, nail care compositions, and preparations for decorative cosmetics, the improvement wherein the composition consists essentially of customary additives and at least one copolymer obtained by
   (i) free-radically initiated copolymerization of a monomer mixture comprising
      (a) 1 to 99.99% by weight of at least one monomer selected from the group consisting of N-vinylimidazoles and diallylamines, optionally in partially or completely quaternized form;
      (b) 0 to 98.99% by weight of at least one neutral or basic water-soluble monomer which is different from (a);
      (c) 0 to 40% by weight of at least one unsaturated acid or unsaturated anhydride,
      (d) 0 to 50% by weight of at least one free-radically copolymerizable monomer which is different from the monomers (a), from the monomers (b) and from the monomers (c); and
      (e) 0.01 to 10% by weight of at least one monomer which acts as crosslinker and has at least two ethylenically unsaturated, nonconjugated double bonds; and
   (ii) subsequent partial or complete quaternization and protonation of the polymer in the case where the monomer (a) is unquaternized or only partially quaternized.

2. The preparation as claimed in claim 1, wherein the protonation as in (ii) takes place during formulation of the preparation.

3. The preparation as claimed in claim 1, wherein monomer (a) is at least one diallylamine derivative of the formula (II),

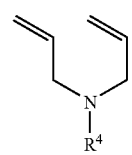

(II)

in which the radical $R^4$ is $C_1$-$C_{24}$ alkyl.

4. The preparation as claimed in claim 1, wherein monomer (a) is at least one N-vinylimidazole derivative of the formula (I),

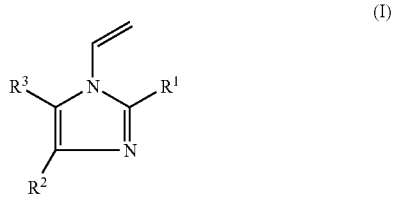

in which the radicals $R^1$ to $R^3$ independently of one another are hydrogen, $C_1$-$C_4$-alkyl or phenyl.

5. The preparation as claimed in claim 1, wherein monomer (b) is at least one N-vinyllactam.

6. The preparation as claimed in claim 1, selected from the group consisting of cosmetic compositions for cleansing the skin.

7. The preparation as claimed in claim 6, selected from the group consisting of soaps, syndets, liquid washing, shower and bath preparations.

8. The preparation as claimed in claim 1, selected from the group consisting of cosmetic compositions for the care and protection of the skin, nailcare compositions, and preparations for decorative cosmetics.

9. The preparation as claimed in claim 8, selected from the group consisting of skincare compositions, personal hygiene care compositions, footcare compositions, sunscreens, repellents, shaving compositions, depilatories, anti-acne compositions, makeup, mascara, lipsticks, eyeshadows, kohl pencils, eyeliners, blushers, powders and eyebrow pencils.

10. The preparation as claimed in claim 9, wherein the skincare compositions are selected from the group consisting of water-in-oil or oil-in-water skin creams, day and night creams, eye creams, antiwrinkle creams, moisturizers, bleaching creams, vitamin creams, skin lotions, care lotions and moisturizing lotions.

11. The preparation as claimed in claim 1, wherein the copolymer is used in the form of a water-in-oil emulsion.

12. The preparation as claimed in claim 11, wherein the copolymer has been polymerized in the emulsion or suspension.

13. The preparation as claimed in claim 12, wherein the oil phase of the emulsion or suspension comprises a cosmetic oil.

14. The skin composition or dermatological preparation of claim 1 wherein a monomer mixture consisting of
- (a) 1 to 99.99% by weight of at least one monomer selected from the group consisting of N-vinylimidazoles and diallylamines, optionally in partially or completely quaternized form;
- (b) 0 to 98.99% by weight of at least one neutral or basic watersoluble monomer which is different from (a);
- (d) 0 to 50% by weight of at least one free-radically copolymerizable monomer which is different from the monomers (a), from the monomers (b), and from unsaturated acids and unsaturated anhydrides;
- (e) 0.01 to 10% by weight of at least one monomer which acts as crosslinker and has at least two ethylenically unsaturated, nonconjugated double bonds;

is employed in the free-radical initiated copolymerization stage (i).

15. The skin composition or dermatological preparation of claim 1 wherein a monomer mixture consisting of
- (a) 1 to 99.99% by weight of at least one monomer selected from the group consisting of N-vinylimidazoles and diallylamines, optionally in partially or completely quaternized form;
- (b) 0 to 98.99% by weight of at least one neutral or basic water-soluble monomer which is different from (a);
- (c) 0 to 40% by weight of at least one unsaturated acid or unsaturated anhydride,
- (d) 0 to 50% by weight of at least one free-radically copolymerizable monomer which is different from the monomers (a), from the monomers (b) and from the monomers (c); and
- (e) 0.01 to 10% by weight of at least one monomer which acts as crosslinker and has at least two ethylenically unsaturated, nonconjugated double bonds;

is employed in the free-radical initiated copolymerization stage (i).

* * * * *

UNITED STATES PATENT AND TRADEMARK OFFICE
CERTIFICATE OF CORRECTION

PATENT NO. : 7,422,735 B1
APPLICATION NO. : 09/604001
DATED : September 9, 2000
INVENTOR(S) : Hössel et al.

Page 1 of 1

It is certified that error appears in the above-identified patent and that said Letters Patent is hereby corrected as shown below:

In claim 14, at column 24, line 13:

"watersoluble"

should read

"water-soluble"

Signed and Sealed this

Tenth Day of March, 2009

JOHN DOLL
*Acting Director of the United States Patent and Trademark Office*